United States Patent
Park et al.

(10) Patent No.: US 11,697,699 B2
(45) Date of Patent: Jul. 11, 2023

(54) METHOD FOR PREDICTING LONG-TERM DURABILITY OF RESIN COMPOSITION FOR PIPING AND OLEFINIC POLYMER USED FOR RESIN FOR PIPING

(71) Applicant: LG Chem, Ltd., Seoul (KR)

(72) Inventors: Sung Hyun Park, Daejeon (KR); Hyun Sup Lee, Daejeon (KR); Jong Sang Park, Daejeon (KR); Joong Soo Kim, Daejeon (KR); Young Suk You, Daejeon (KR); Dae Sik Hong, Daejeon (KR); Myung Han Lee, Daejeon (KR)

(73) Assignee: LG Chem, Ltd.

( * ) Notice: Subject to any disclaimer, the term of this patent is extended or adjusted under 35 U.S.C. 154(b) by 491 days.

(21) Appl. No.: 16/647,751

(22) PCT Filed: Sep. 28, 2018

(86) PCT No.: PCT/KR2018/011478
§ 371 (c)(1),
(2) Date: Mar. 16, 2020

(87) PCT Pub. No.: WO2019/066516
PCT Pub. Date: Apr. 4, 2019

(65) Prior Publication Data
US 2020/0223964 A1    Jul. 16, 2020

(30) Foreign Application Priority Data

Sep. 29, 2017 (KR) .......................... 10-2017-0127803
Feb. 6, 2018 (KR) .......................... 10-2018-0014323

(51) Int. Cl.
| | |
|---|---|
| G01N 3/36 | (2006.01) |
| G01N 33/44 | (2006.01) |
| C08L 23/08 | (2006.01) |
| C08F 210/16 | (2006.01) |
| G01N 3/56 | (2006.01) |
| C08F 110/04 | (2006.01) |

(52) U.S. Cl.
CPC ............. *C08F 210/16* (2013.01); *G01N 3/56* (2013.01); *G01N 33/442* (2013.01); *C08F 110/04* (2013.01); *C08L 23/08* (2013.01); *G01N 2203/0071* (2013.01)

(58) Field of Classification Search
CPC ....... G01N 3/56; G01N 33/44; C08L 23/0815
See application file for complete search history.

(56) References Cited

U.S. PATENT DOCUMENTS

| | | | |
|---|---|---|---|
| 5,004,778 | A | 4/1991 | Waagen et al. |
| 6,201,069 | B1 | 3/2001 | Fukazawa et al. |
| 2013/0011716 | A1 | 1/2013 | Sano et al. |
| 2017/0029538 | A1 | 2/2017 | Song et al. |
| 2019/0086308 | A1 | 3/2019 | Lee et al. |

FOREIGN PATENT DOCUMENTS

| | | |
|---|---|---|
| CN | 1215497 A | 4/1999 |
| CN | 101423573 A | 5/2009 |
| CN | 102812076 A | 12/2012 |
| EP | 0942020 A1 | 9/1999 |
| EP | 0892979 B1 | 5/2003 |
| EP | 3517976 A1 | 7/2019 |
| JP | S63308049 A | 12/1988 |
| JP | H08027211 A | 1/1996 |
| JP | H11230962 A | 8/1999 |
| JP | 2004169037 A | 6/2004 |
| JP | 3867236 B2 | 1/2007 |
| JP | 2017516880 A | 6/2017 |
| JP | 2019529950 A | 10/2019 |
| WO | 9911684 A1 | 3/1999 |

OTHER PUBLICATIONS

Aya, T. et al., "Amorphous Structure Control and Mechanical Characteristics of Polyolefin by Blending Petroleum Resin", Kobunshi Ronbunshu, Dec. 2005, pp. 579-584, vol. 62, No. 12. (Providing English Translation of Abstract only).
Cheng, J. et al., "Chain Entanglements and Mechanical Behavior of High Density Polyethylene", Journal of Engineering Materials and Technology, Jan. 2010, pp. 011016-1-011016-7, vol. 132.
Seguela, R. "Critical Review of the Molecular Topology of Semicrystalline Polymers: The Origin and Assessment of Intercrystalline Tie Molecules and Chain Entanglements", Wiley InterSciense, Dec. 2004, pp. 1729-1748, vol. 43.
Adib et al., The effect of microstructure on the slow crack growth resistance in polyethylene resins, Polymer Engineering and Science, Jul. 2014, pp. 1018-1023, vol. 55, No. 5, XP055627676.
Aiba et al., Effect of ultra-high molecular weight species in high-density polyethylenes on the resistance to creep failure by a surface active agent, Polymer Degradation and Stability, Aug. 1998, pp. 1-8, vol. 61, XP004294406.
Extended European Search Report including Written Opinion for Application No. EP18860648.7, dated Dec. 8, 2020, pp. 1-13.
Search Report dated Mar. 9, 2022 from the Office Action for Chinese Application No. 201880057741.X dated Mar. 15, 2022, 2 pages.

(Continued)

*Primary Examiner* — Caixia Lu
(74) *Attorney, Agent, or Firm* — Lerner David LLP (57) ABSTRACT

A method for evaluating long-term durability of a resin for piping is provided. Unlike the conventional FNCT evaluation method requiring a long period of time, the method disclosed herein is capable of predicting long-term durability of a resin for piping in a short time, by a simple calculation using a content of tie molecules, an entanglement molecular weight ($M_e$) and a content of ultrahigh molecular weight components. In addition, the olefinic polymer is configured to have a predetermined relationship in relation to the content of tie molecules, the entanglement molecular weight ($M_e$) and the content of ultrahigh molecular weight components, whereby the polymer of the present application can be used in the manufacture of a heating pipe requiring excellent long-term durability.

7 Claims, 1 Drawing Sheet

(56) References Cited

OTHER PUBLICATIONS

Cazenave et al., "Short-term Mechanical and Structural Approaches for the Evaluation of Polyethylene Stress Crack Resistance", Polymer, Mar. 2006, vol. 47, pp. 3904-3914.
International Search Report from Application No. PCT/KR2018/011478 dated Jan. 2, 2019, 3 pages.
Sardashti, "Methodologies for Obtaining Reliable Indicators for the Environmental Stress Cracking Resistance of Polyethylene", A Thesis for the Degree of Doctor of Philosophy, University of Waterioo, Feb. 2014, pp. 1-214.

METHOD FOR PREDICTING LONG-TERM DURABILITY OF RESIN COMPOSITION FOR PIPING AND OLEFINIC POLYMER USED FOR RESIN FOR PIPING

CROSS-REFERENCE TO RELATED APPLICATIONS

The present application is a national phase entry under 35 U.S.C. § 371 of International Application No. PCT/KR2018/011478 filed on Sep. 28, 2018 which claims priority from Korean Patent Application No. 10-2017-0127803 filed on Sep. 29, 2017 and Korean Patent Application No. 10-2018-0014323 filed on Feb. 6, 2018, with the Korean Intellectual Property Office, the disclosures of which are incorporated herein by reference in their entirety.

TECHNICAL FIELD

The present application relates to a method for predicting long-term durability of a resin for piping or a composition comprising the resin. The present application also relates to an olefinic polymer contained in a composition which can be used for forming a resin for piping.

BACKGROUND ART

Since plumbing pipes used in heating pipes are constructed inside buildings, they should have excellent long-term durability so as to prevent water leakage due to cracks. Known methods for evaluating long-term durability of plumbing pipes are ISO 9080 and ISO 16770, and the like. ISO 9080 is a method of estimating the pressure expected to cause cracks over 50 years by measuring the crack occurrence time over one year according to the temperature and pressure of water passing through a pipe and extrapolating this. Products with long-term durability recognized by ISO 9080 have environmental stress crack resistance (ESCR) of about 2,000 hours or more, as measured at a stress of 4.0 MPa and a temperature of 80° C. by full notch creep test (FNCT) according to ISO 16770. That is, according to the above method, the relevant product has durability to the extent that the sample breaks after 2,000 hours or more must elapse. However, there is a problem that it takes at least 3 months to 1 year or more to perform the two methods. Therefore, a method capable of predicting long-term durability in a quick way is required, so that product development time can be shortened by selecting a sample to be measured for long-term durability among various samples in the product development stage.

Furthermore, it is considered that the long-term durability of the pipe used in the above application is affected by the characteristics of the resin used for forming the pipe. Therefore, there is a need for a polymer-related design standard that can ensure long-term durability of the pipe.

DISCLOSURE

Technical Problem

It is one object of the present application to provide a method for predicting long-term durability of a resin composition for piping in a short time.

It is another object of the present application to provide a method for comparatively evaluating long-term durability for a plurality of resin compositions for piping.

It is another object of the present application to provide a polymer which can be used for manufacturing a heater-plumbing pipe having excellent long-term durability.

It is another object of the present application to provide a resin composition for heater-piping having excellent environmental stress crack resistance.

The above objects and other objects of the present application can be all solved by the present application which is described in detail below.

Technical Solution

In one example concerning the present application, the present application relates to a method for predicting or evaluating long-term durability of a resin composition for piping.

In the present application, the sample to be predicted or evaluated may be a resin or a resin composition containing other components. Furthermore, in the present application, the resin (composition) for piping may mean a resin (composition) used in a pipe forming a moving path of a fluid or the like, and may mainly mean a resin (composition) for heater-piping.

The long-term durability prediction method of the present application uses a tie molecule, an entanglement molecular weight (Me) and a mass-average molecular weight (Mw) as factors for predicting long-term durability.

In the present application, the tie molecule, which is one of the factors used for predicting long-term durability, means a polymer molecule connecting crystals of an amorphous polymer resin. In the amorphous polymer molecule, crystals of lamellar structures are formed by chain folding below a crystallization temperature. At this time, if a polymer structure capable of forming a defect in the crystal structure, for example, an α-olefin or an LCB (long chain branch), is present, the relevant moiety does not form crystals and remains amorphous. On the other hand, the lamellar structures can be formed in the moiety where no α-olefin or LCB structure is present, so that one polymer chain can form crystalline-amorphous-crystalline structures. In such a structure, the amorphous moiety serves to connect the crystal to the crystal, which is referred to as a tie molecule. As the polymer molecule has a high molecular weight and thus the length of the polymer chain is longer, the probability that the tie molecules will be produced increases. As described above, the higher the content of the tie molecules is, the stronger the connection between the crystal structures is, and thus it is considered that crack generation and propagation become difficult. Taking this point into consideration, in the present application, the content of tie molecules is used as one factor for predicting long-term durability. At this time, the content of tie molecules means a % ratio, that is, a wt %, of the polymer molecules forming the tie molecules based on the weight 100 of the entire polymer molecule contained in the resin composition. The content of tie molecules can be determined as described below.

When one polymer chain is tangled with the surrounding polymers or itself to form an entanglement point functioning as a physical crosslink, the entanglement molecular weight ($M_e$), which is another factor used in the present application method, means an average molecular weight between such entanglement points. As the polymer molecule has a high molecular weight and thus the length of the polymer chain is longer, the probability that entanglement points will be generated increases, so that the entanglement molecular weight decreases. The smaller the entanglement molecular weight, the greater the entanglement degree of the polymer, and thus it is considered that the resistance to external force increases. Taking this point into consideration, in the present application, the entanglement molecular weight is used as one of factors of long-term durability prediction. The entanglement molecular weight can be measured as described below.

Another of the factors used in the long-term durability prediction of the present application is the content of an ultrahigh molecular weight component. At this time, the ultrahigh molecular weight means a case where the mass average molecular weight (Mw) is 1,000,000 or more, and the content of the ultrahigh molecular weight component means a % ratio, that is, a wt %, of the polymer having a mass average molecular weight of 1,000,000 or more based on the weight 100 of the entire polymer contained in the resin composition. The higher the content of the ultrahigh molecular weight component, the larger the number of polymer molecules having a longer polymer chain length, and thus it is considered that the entanglement of the polymer chain or the content of tie molecules increases. Taking this point into consideration, in the present application, the content of the ultrahigh molecular weight component is used as one factor for predicting the long-term durability. The content of the ultrahigh molecular weight component can be measured as described below.

According to the present application in which the above factors are used for the long-term durability measurement of a resin composition as a sample, the long-term durability of the resin composition can be predicted or evaluated in a short time even if a small amount of a sample is used.

Specifically, the method according to the present application can predict or evaluate the long-term durability of a resin composition as a sample by using the following equation.

$$\text{Long-term durability predicted value of resin composition} = a \times (X)^b \times (Y)^c \times (Z)^d \quad \text{[Equation]}$$

In Equation above, a=386,600, b=4.166, c=−1.831, and d=1.769. Furthermore, X, Y and Z are values relating to molecular characteristics that can be measured in a resin composition as a sample, respectively. Specifically, X means a content (wt %) of tie molecules, Y means an entanglement molecular weight (g/mol), and Z means a content (wt %) of a component having a mass average molecular weight (Mw) of 1,000,000 or more. At this time, X, Y and Z are used as dimensionless constants excluding the units.

The inventors of the present application have confirmed that the predicted value concerning the long-term durability calculated according to Equation above is very similar to the environmental stress crack resistance evaluation result actually measured by the full notch creep test (FNCT) according to ISO 16770 at 4.0 MPa and 80° C. Therefore, if a predicted value of the long-term durability of a resin composition as a sample is calculated according to the present application, the long-term durability of a resin composition for piping can be predicted or evaluated in a short time by only simple calculation without performing the durability evaluation over a long period of time such as ISO 9080 or ISO 16770.

In the present application, the predicted value calculation of long-term durability can be made for a plurality of samples. In this case, it can be determined that the long-term durability of the sample having the largest calculated value is the most excellent.

In the present application, a sample to be predicted or evaluated for long-term durability, that is, a resin composition may comprise a homopolymer formed from one monomer component and/or a copolymer formed from a plurality of different monomer components. Then, the resin composition may also comprise one or more homopolymers or copolymers.

In one example, the resin composition as the sample may comprise a polyolefin. The kind of the polyolefin is not particularly limited. For example, the polyolefin may be a polymer formed from ethylene, butylene, propylene, and/or α-olefinic monomers. The kind of the α-olefinic monomer is not particularly limited. For example, 1-butene, 1-pentene, 4-methyl-1-pentene, 1-hexene, 1-heptene, 1-octene, 1-decene, 1-undecene, 1-dodecene, 1-tetradecene, 1-hexadecene, 1-octadecene or 1-eicosene, and the like can be used, without being particularly limited thereto.

In one example concerning the present application, the present application relates to an olefinic polymer. The polymer can be used in a pipe forming a moving path of a fluid or the like, and can be mainly used for forming a heating pipe. Since the polymer satisfies predetermined conditions and/or configurations to be described below, it has excellent long-term durability which can be confirmed, for example, through evaluation of environmental stress crack resistance.

In the present application, as design factors of the olefinic polymer, a content of tie molecules, an entanglement molecular weight (Me) and a content of an ultrahigh molecular weight component can be used.

In the present application, the tie molecule, which is one of the design factors of a polymer, means a polymer molecule connecting crystals of an amorphous polymer resin. In the amorphous polymer molecule, crystals of lamellar structures are formed by chain folding below a crystallization temperature. At this time, if a polymer structure capable of forming a defect in the crystal structure, for example, an α-olefin or an LCB (long chain branch), is present, the relevant moiety does not form crystals and remains amorphous. On the other hand, the lamellar structures can be formed in the moiety where no α-olefin or LCB structure is present, so that one polymer chain can form crystalline-amorphous-crystalline structures. In such a structure, the amorphous moiety serves to connect the crystal to the crystal, which is referred to as a tie molecule. As the polymer molecule has a high molecular weight and thus the length of the polymer chain is longer, the probability that the tie molecules will be produced increases. As described above, the higher the content of the tie molecules is, the stronger the connection between the crystal structures is, and thus it is considered that crack generation and propagation become difficult. Taking this into consideration, in the present application, the content of tie molecules is used as one factor of the polymer design used for the above application. At this time, the content of tie molecules means a % ratio, that is, a wt %, of the (polymer) component forming the tie molecules based on the weight 100 of the entire polymer molecule contained in the resin composition. The content of tie molecules can be determined as described below.

When one polymer chain is tangled with the surrounding polymers or itself to form an entanglement point functioning as a physical crosslink, the entanglement molecular weight ($M_e$), which is another factor used in the present application, means an average molecular weight between such entanglement points. As the polymer molecule has a high molecular weight and thus the length of the polymer chain is longer, the probability that entanglement points will be generated increases, so that the entanglement molecular weight decreases. The smaller the entanglement molecular weight, the greater the entanglement degree of the polymer, and thus it is considered that the resistance to external force increases. Taking this point into consideration, the present application uses the entanglement molecular weight as one factor in the polymer design used for the above application. The entanglement molecular weight can be measured as described below.

Another of the factors used in the present application is the content of an ultrahigh molecular weight component. At this time, the ultrahigh molecular weight means a case where the mass average molecular weight (Mw) is 1,000,000 or more, and the content of the ultrahigh molecular weight component means a % ratio, that is, a wt %, of the (polymer) component having a mass average molecular weight of 1,000,000 or more based on the weight 100 of the entire polymer. The higher the content of the ultrahigh molecular weight component, the larger the number of polymer molecules having a longer polymer chain length, and thus it is considered that the entanglement of the polymer chain or the content of tie molecules increases. Taking this point into consideration, the present application uses the content of the ultrahigh molecular weight component as one factor of the polymer design used for the above application. The content of the ultrahigh molecular weight component can be measured as described below.

The inventors of the present application have confirmed that when the olefinic polymer is designed to satisfy a predetermined relationship with regard to such factors, it is possible to provide a resin for heater-piping having excellent long-term durability. Specifically, the olefinic polymer of the present application may be an olefinic polymer satisfying at least two conditions of the following conditions [A] to [C].

[A] A content of tie molecules is 10 wt % or more

[B] An entanglement molecular weight (Me) is 17,000 g/mol or less

[C] A content of a component having a mass average molecular weight (Mw) of 1,000,000 or more is 2.5 wt % or more When at least two conditions of [A] to [C] are satisfied, it is possible to show excellent long-term durability characteristics in the environmental stress crack resistance (ESCR) evaluation measured by the full notch creep test (FNCT) according to ISO 16770 at 4.0 MPa and 80° C. For example, time characteristics to be described below can be satisfied.

In one example, the polymer may further satisfy the condition that the content of tie molecules is 30 wt % or less, 25 wt % or less, or 20 wt % or less with regard to the above condition [A]. Upon designing the polymer for the predetermined application, in consideration of the significance that the content of tie molecules as described above has, an increase in the content can be considered. To increase the content of tie molecules, the density of the polymer should be lowered or the content of the higher molecular weight component should be increased. However, if the density decreases, the pressure-resistant performance of the final pipe product declines, and if the content of the polymer component increases, the viscosity increases, whereby there is a problem that the processability deteriorates, so that it is preferable to control the content of tie molecules in the above content range.

In another example, the polymer may further satisfy the condition that the entanglement molecular weight (Me) is 1000 g/mol or more, 2000 g/mol or more, 3000 g/mol or more, 4000 g/mol or more, or 5000 g/mol or more with regard to the above condition [B]. Upon designing the polymer for the predetermined application, in consideration of the significance that the content of the entanglement molecular weight as described above has, a decrease in the molecular weight can be considered. However, when the entanglement molecular weight is too low, the content of the high molecular weight component becomes high, so that the processability is lowered. In addition, since breakage easily occurs in the stretching process for adjusting dimensions and the like such as a diameter or a thickness after extruding the produced pipe, there is also a need to stretch it at a low speed, so that there is a problem that productivity is lowered. Therefore, it is preferable to have molecular weight more than the said range.

In another example, the polymer may further satisfy the condition that the content of the component having a mass average molecular weight (Mw) of 1,000,000 or more is 20 wt % or less, 15 wt % or less, or 10 wt % or less with regard to the above condition [C]. If the content of the ultrahigh molecular weight component exceeds the above range, the processability may be deteriorated.

In another example, the polymer may satisfy all of the conditions [A] to [C]. When all the three conditions are satisfied, more excellent long-term durability can be ensured.

The kind of the monomer for forming the olefinic polymer is not particularly limited. For example, the olefinic polymer may be formed from a monomer mixture comprising ethylene, butylene, propylene, or α-olefinic monomers. That is, the polymer of the present application may be one prepared by polymerizing one or more monomers of the above monomers. At this time, the kind of the α-olefinic monomer is not particularly limited. For example, 1-butene, 1-pentene, 4-methyl-1-pentene, 1-hexene, 1-heptene, 1-octene, 1-decene, 1-undecene, 1-dodecene, 1-tetradecene, 1-hexadecene, 1-octadecene or 1-eicosene, and the like can be used, without being particularly limited thereto.

In one example, the monomer mixture may comprise two or more monomers selected from ethylene, butylene, propylene, and α-olefinic monomers. At this time, the two or more monomers contained in the monomer mixture may be different from each other, where the kind of the α-olefinic monomer is the same as those listed above.

In one example, the olefinic polymer may comprise ethylene as a main component. In the present application, in relation to the components of the polymer, the main component monomer may means a case where the content of the main component monomer exceeds 50 wt % based on the content 100 of the total monomers used for forming the polymer. The upper limit of the main component monomer content is not particularly limited, but may be, for example, 95 wt % or less, 90 wt % or less, 85 wt % or less, 80 wt % or less, 75 wt % or less, or 70 wt % or less. In this case, the monomer mixture may comprise one or more monomers selected from butylene, propylene, and α-olefinic monomers as a copolymerizable monomer, in addition to ethylene as the main component. The copolymerizable monomer may be used in the monomer mixture as much as the remaining content other than the content of ethylene as the main monomer.

In one example, 1-butene (1-C4) may be used as the copolymerizing monomer for forming the olefinic polymer. Specifically, a monomer having a short length, for example, 1-butene may be used due to influences of the characteristics of the polymerization equipment or the supply and demand of raw materials, and the like. However, in such a case, the long-term durability may be lowered as compared with a product produced using a relatively long copolymerizing monomer, for example, 1-hexene (1-C6) or 1-octene (1-C8), and the like. However, when the above-described conditions of the present application are satisfied, superior long-term durability can be ensured even when a copolymerizing monomer having a relatively short length such as 1-butene is used. The content of 1-butene to be used is not particularly limited, but may be used so as to satisfy a range of about 7.0 to 10.1/1,000 C as a result of FT-IR analysis.

The polymer satisfying the above conditions and configuration may have environmental stress cracking resistance (ESCR) of 1500 hours or more measured by the full notch creep test (FNCT) according to ISO 16770 at 4.0 MPa and 80° C. More preferably, the polymer may have environmental stress cracking resistance (ESCR) of 2000 hours to 8000 hours measured by the full notch creep test (FNCT) according to the same conditions and method.

Advantageous Effects

According to one example of the present application, a method capable of predicting long-term durability of a resin for piping in a short time using a small amount of a sample can be provided. Also, according to the present application, since the long-term durability of the resin for piping can be evaluated in a short time, a polymer structure having excellent long-term durability can be usefully designed and a sample that is worth actually measuring long-term durability can be selected in a short time, so that the efficiency of the product development stage can be improved and the development time can be shortened. In addition, according to the present application, an olefinic polymer structure having excellent long-term durability can be usefully designed, and a plumbing pipe having excellent long-term durability can be provided.

BEST MODE

Figure 1:
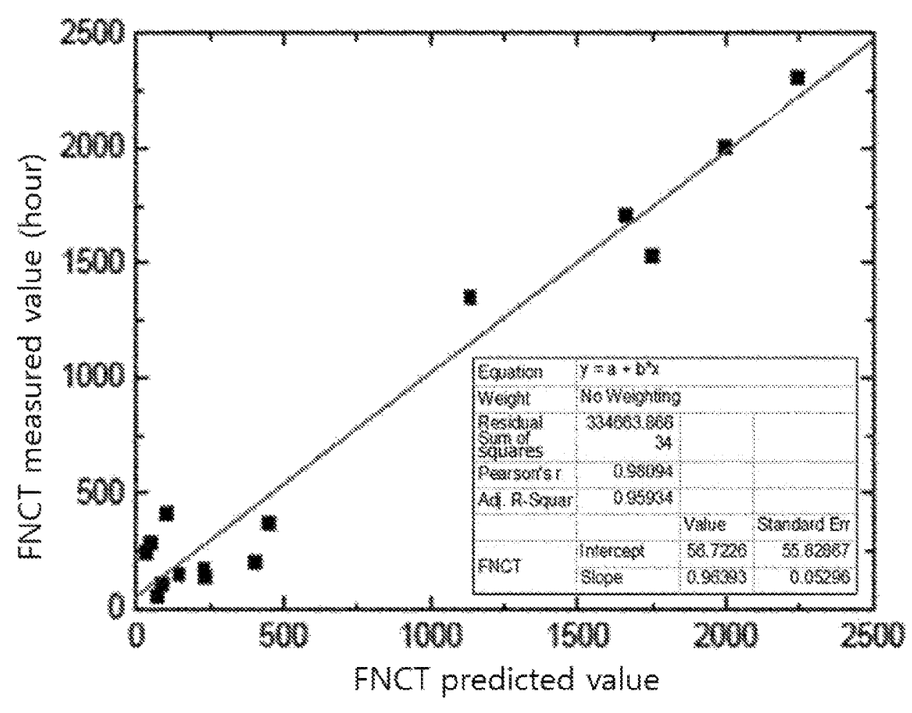
FIGURE is a graph showing the correlation between FNCT measured values of the resin used in a Preparation Example and FNCT predicted values calculated for each resin of the present application examples corresponding to the Preparation Example.

Hereinafter, the present application will be described in detail through examples. However, the protection scope of the present application is not limited by the following examples.

Experimental Example 1: Experimental Example on Long-Term Durability Prediction

The relevant physical properties and the like measured in the following experimental examples were measured according to the following methods.

Measuring Method

FNCT (full notch creep test) measured value: For the resins of Preparation Examples 1 to 15 prepared below, a full notch creep test was performed according to ISO 16770 at a stress of 4.0 MPa and a temperature of 80° C. Specifically, a specimen for performing the FNCT was a rectangular parallelepiped having a size of 10×10×100 mm, which was obtained by milling a plate having a thickness of 15 mm. Then, notches having a depth of 1.5 mm were formed on four sides of the specimen, a stress of 4.0 MPa was applied to the specimen in a 10% Igepal solution at 80° C., and then the time taken until the specimen was broken was measured. Based on the measured time, the properties of the resins were qualitatively classified according to the following criteria.

<Qualitative Classification of FNCT Measured Values>
above 2,000 hours: excellent
1,500 hours to less than 2,000 hours: somewhat excellent
1,000 hours to less than 1,500 hours: normal
400 hours to less than 1,000 hours: somewhat poor
less than 400 hours: poor Content of tie molecules: The molecular weight distribution, melting point (Tm) and mass fraction crystallinity were calculated in the following methods, and the content of tie molecules was calculated from these values.

Molecular weight distribution: 10 mg of a sample to be measured was dissolved in 1,2,4-trichlorobenzene containing 0.0125% of BHT at 160° C. for 10 hours and pretreated using PL-SP260 from Agilent, and a GPC curve was obtained using PL-GPC220 as GPC (gel permeation chromatography) for high temperature.

Melting point and mass fraction crystallinity: 5 mg of a sample to be measured was placed on an Al pan, covered with an Al lid, and then punched and sealed, and it was heated from 50° C. to 190° C. at 10° C./min using DSC Q20 from TA (Cycle 1), and cooled to 50° C. at 10° C./min after isothermal treatment at 190° C. for 5 minutes, and then heated again to 190° C. at 10° C./min after isothermal treatment at 50° C. for 5 minutes (Cycle 2). The melting point and mass fraction crystallinity were calculated from the temperature (Tm) and area (ΔH) of the DSC curve peak in the range of 60° C. to 140° C. in Cycle 2.

Tm: temperature of DSC curve peak
Mass fraction crystallinity: ΔH/293.6×100 (293.6: ΔH at 100% crystal)

Content calculation of tie molecules: The content of tie molecules was calculated from the area of the tie molecule distribution graph in which the x-axis was the molecular weight M and the y-axis was represented by n·P·dM. The corresponding graph is calculated from the GPC curve and DSC measurement results. With regard to the y-axis, n is the number of the polymer molecules having a molecular weight of M, which can be obtained as (dw/d log Mw)/M from the data of the GPC curve in which the x-axis is log Mw and the y-axis is dw/d log Mw. In addition, the P is a probability that the polymer molecules having a molecular weight of M form tie molecules, which can be calculated from the following equations 1 to 3, and the dM is an interval between the x-axis data (molecular weight M) of the GPC curve.

$$P = \frac{1}{3} \frac{\int_{2l_c+l_a}^{\infty} r^2 \exp(-b^2 r^2) dr}{\int_0^{\infty} r^2 \exp(-b^2 r^2) dr} \quad \text{[Equation 1]}$$

In Equation 1 above, r is an end-to-end distance of a random coil, $b^2$ is $3/2r^2$, $l_c$ is a crystal thickness, which is obtained from Equation 2 below, and $l_a$ is an amorphous thickness, which is obtained from Equation 3 below.

$$T_m = T_m^o \left(1 - \frac{2\sigma_e}{\Delta h_m l_c}\right) \quad \text{[Equation 2]}$$

In Equation 2 above, $T°_m$ is 415K, $\sigma_e$ is 60.9×10⁻³ J/m², and $\Delta h_m$ is 2.88×10³ J/m³.

$$l_a = \rho_c l_c (1-\omega^c)/\rho_a \omega^c \quad \text{[Equation 3]}$$

In Equation 3 above, pc is a crystal density, which is 1,000 kg/m³, $\rho_a$ is a density of amorphous phase, which is 852 kg/m³, $\omega^c$ is weight fraction crystallinity, which is confirmed from DSC results.

Calculation of entanglement molecular weight (Me): Using a rotary rheometer, a storage elastic modulus and a loss elastic modulus of each sample were measured under conditions of a temperature of 150° C. to 230° C., an angular frequency of 0.05 to 500 rad/s and a strain of 0.5%, and from the plateau elastic modulus (GN0) thus obtained, the entanglement molecular weight was calculated according to Theoretical Equation below. However, in Theoretical Equation below, p means a density (kg/m³), R is the gas constant (8.314 Pa·m³/mol·K) and T is the absolute temperature (K).

$$M_e = (\rho RT)/G_N^0 \quad \text{[Theoretical Equation]}$$

Content measurement and calculation of ultrahigh molecular weight component: In the molecular weight distribution analysis result of the sample, the area ratio (%) of the portion having a molecular weight of 1,000,000 or more relative to the total area was calculated.

Long-term durability predicted value: The predicted value of long-term durability was calculated by substituting the values obtained from the above into the following equation.

$$\text{Long-term durability predicted value of resin composition} = a \times (X)^b \times (Y)^c \times (Z)^d \quad \text{[Equation]}$$

However, in Equation above, a=386,600, b=4.166, c=−1.831, and d=1.769, X, Y and Z mean, in a resin composition as a sample, a content (wt %) of tie molecules, an entanglement molecular weight (g/mol) and a content (wt %) of a component having a mass average molecular weight (Mw) of 1,000,000 or more, respectively. At this time, in Equation above, X, Y and Z are used as dimensionless constants excluding the units.

Based on the predicted value calculated from Equation above, the characteristics of the resin were classified qualitatively by the following criteria.

<Qualitative Classification of Predicted Values>
above 2,000: excellent
1,500 to less than 2,000: somewhat excellent
1,000 to less than 1,500: normal
400 to 1,000: somewhat poor
less than 400: poor

PREPARATION EXAMPLES

A resin as a target for long-term durability measurement was prepared as follows. Then, the time was measured according to the FNCT (full notch creep test). The results are shown in Table 1.

Preparation Example 1: In a hexane slurry CSTR process, the resin was polymerized while supplying ethylene, hydrogen and 1-butene at a predetermined input rate using a metallocene catalyst. The prepared resin had a density of 0.9396 g/cm³ as measured according to ASTM D 1505 and an MI (melt index) of 0.26 as measured under conditions of 190° C. and 2.16 kg/10 min according to ASTM D 1238.

Preparation Example 2: A resin was prepared in the same manner as in Preparation Example 1, except that the input rate of the raw materials was controlled differently. The density of the prepared resin was 0.9392 g/cm³ and the MI was 0.34.

Preparation Example 3: A resin was prepared in the same manner as in Preparation Example 1, except that the input rate of the raw materials was controlled differently. The density of the prepared resin was 0.9358 g/cm³ and the MI was 0.75.

Preparation Example 4: A resin was prepared in the same manner as in Preparation Example 1, except that the input rate of the raw materials was controlled differently. The density of the prepared resin was 0.9359 g/cm³ and the MI was 0.47.

Preparation Example 5: A resin was prepared in the same manner as in Preparation Example 1, except that the input rate of the raw materials was controlled differently. The density of the prepared resin was 0.9363 g/cm³ and the MI was 0.27.

Preparation Example 6: A resin was prepared in the same manner as in Preparation Example 1, except that the input rate of the raw materials was controlled differently. The density of the prepared resin was 0.9396 g/cm³ and the MI was 0.32.

Preparation Example 7: A resin was prepared in the same manner as in Preparation Example 1, except that the input rate of the raw materials was controlled differently. The density of the prepared resin was 0.9365 g/cm³ and the MI was 0.60.

Preparation Example 8: A resin was prepared in the same manner as in Preparation Example 3, except that the input rate of the raw materials was controlled differently. The density of the prepared resin was 0.9367 g/cm³ and the MI was 0.47.

Preparation Example 9: A resin was prepared in the same manner as in Preparation Example 1, except that the input rate of the raw materials was controlled differently. The density of the prepared resin was 0.9369 g/cm³ and the MI was 0.38.

Preparation Example 10: A resin was prepared in the same manner as in Preparation Example 1, except that the input rate of the raw materials was controlled differently. The density of the prepared resin was 0.9364 g/cm³ and the MI was 0.48.

Preparation Example 11: A resin was prepared in the same manner as in Preparation Example 1, except that the density was 0.9362 g/cm³ and the MI measured under the same conditions was 0.43.

Preparation Example 12: A resin was prepared in the same manner as in Preparation Example 1 except that the density was 0.9363 g/cm³ and the MI measured under the same conditions was 0.26.

Preparation Example 13: A resin was prepared in the same manner as in Preparation Example 1, except that the density was 0.9362 g/cm³ and the MI measured under the same conditions was 0.44.

Preparation Example 14: A resin was prepared in the same manner as in Preparation Example 1, except that the density was 0.9357 g/cm³ and the MI measured under the same conditions was 0.25.

Preparation Example 15: A resin was prepared in the same manner as in Preparation Example 1, except that the density was 0.9363 g/cm³ and the MI measured under the same conditions was 0.39.

Examples

Example 1

For the sample prepared in Preparation Example 1, the content of tie molecules, the entanglement molecular weight, and the content of the ultrahigh molecular weight component were measured according to the above methods, and the predicted value concerning long-term durability was calculated by substituting them into Equation according to the present application. The result is as shown in Table 2.

Examples 2 to 15

The contents of tie molecules, the entanglement molecular weights and the contents of the ultrahigh molecular weight components were measured and the predicted values concerning the durability were calculated, in the same manner as in Example 1, except that in Examples 2 to 15, the resins prepared in accordance with Preparation Examples 2 to 15 in this order were used, respectively.

TABLE 1

| Preparation Example | FNCT measured value (hour) | Remark |
|---|---|---|
| 1 | 2310 | Excellent |
| 2 | 376 | Poor |
| 3 | 59 | Poor |
| 4 | 206 | Poor |
| 5 | 2000 | Excellent |
| 6 | 1710 | Somewhat excellent |
| 7 | 244 | Poor |
| 8 | 285 | Poor |
| 9 | 416 | Somewhat poor |
| 10 | 114 | Poor |
| 11 | 138 | Poor |
| 12 | 1537 | Somewhat excellent |
| 13 | 155 | Poor |
| 14 | 1354 | Normal |
| 15 | 168 | Poor |

TABLE 2

| Example | Content of tie molecules (%) | Me (g/mol) | Content of ultrahigh molecular weight component (%) | Long-term durability predicted value | Remark |
|---|---|---|---|---|---|
| 1 | 12.4 | 13900 | 2.8 | 2226 | Excellent |
| 2 | 10.6 | 19500 | 2.4 | 474 | Somewhat poor |
| 3 | 9.6 | 36700 | 2.0 | 71 | Poor |
| 4 | 11.2 | 25600 | 2.6 | 418 | Somewhat poor |
| 5 | 11.3 | 15800 | 3.7 | 1958 | Somewhat excellent |
| 6 | 8.2 | 11700 | 5.2 | 1629 | Somewhat excellent |
| 7 | 9.5 | 35900 | 1.2 | 29 | Poor |
| 8 | 9.8 | 28200 | 1.2 | 51 | Poor |
| 9 | 9.5 | 23300 | 1.6 | 106 | Poor |
| 10 | 10.2 | 25100 | 1.3 | 86 | Poor |
| 11 | 11.0 | 23800 | 1.8 | 231 | Poor |
| 12 | 11.2 | 12500 | 2.8 | 1770 | Somewhat excellent |
| 13 | 10.6 | 25300 | 1.6 | 144 | Poor |
| 14 | 11.9 | 15100 | 2.3 | 1138 | Normal |
| 15 | 11.8 | 22800 | 1.4 | 215 | Poor |

Comparing the FNCT measured values in Table 1 with the dimensionless calculated values in Table 2, it can be seen that their values are very similar. Then, it can be confirmed that the measured values and the calculated values can be evaluated very similarly even in the qualitative classification. Actually, it is also confirmed in FIGURE that the X-axis and the Y-axis have a strong linear correlation. That is, the durability prediction method of the present application can replace the conventional FNCT measurement method. In other words, the method according to the present application can evaluate the durability of the resin (composition) for piping in a short time only by measuring the molecular weight and the like, even without going through a testing period of several months or more.

Experimental Example 2: Confirmation of Suitability as Polymer for Heater-Piping The relevant physical properties and the like measured in the following experimental examples were measured according to the following methods.

Measuring Method

FNCT (full notch creep test) measured value: For the polymers of Preparation Examples 1 to 14 prepared below, a full notch creep test was performed according to ISO 16770 at a stress of 4.0 MPa and a temperature of 80° C. Specifically, a specimen for performing the FNCT was a rectangular parallelepiped having a size of 10×10×100 mm, which was obtained by milling a plate having a thickness of 15 mm. Then, notches having a depth of 1.5 mm were formed on four sides of the specimen, a stress of 4.0 MPa was applied to the specimen in a 10% Igepal solution at 80° C., and then the time taken until the specimen was broken was measured. Based on the measured time, the properties of the resins were qualitatively classified according to the following criteria.

<Qualitative Classification of FNCT Measured Values>
above 2,000 hours: excellent
1,500 hours to less than 2,000 hours: somewhat excellent
1,000 hours to less than 1,500 hours: normal
400 hours to less than 1,000 hours: somewhat poor
less than 400 hours: poor Content of tie molecules: The molecular weight distribution, melting point (Tm) and mass fraction crystallinity were calculated in the following methods, and the content of tie molecules was calculated from these values.

Molecular weight distribution: 10 mg of a sample to be measured was dissolved in 1,2,4-trichlorobenzene containing 0.0125% of BHT at 160° C. for 10 hours and pretreated using PL-SP260 from Agilent, and a GPC curve was obtained using PL-GPC220 as GPC (gel permeation chromatography) for high temperature.

Melting point and mass fraction crystallinity: 5 mg of a sample to be measured was placed on an Al pan, covered with an Al lid, and then punched and sealed, and it was heated from 50° C. to 190° C. at 10° C./min using DSC Q20 from TA (Cycle 1), and cooled to 50° C. at 10° C./min after isothermal treatment at 190° C. for 5 minutes, and then heated again to 190° C. at 10° C./min after isothermal treatment at 50° C. for 5 minutes (Cycle 2). The melting point and mass fraction crystallinity were calculated from the temperature (Tm) and area (ΔH) of the DSC curve peak in the range of 60° C. to 140° C. in Cycle 2.

Tm: temperature of DSC curve peak

Mass fraction crystallinity: ΔH/293.6×100 (293.6: ΔH at 100% crystal)

Content calculation of tie molecules: The content of tie molecules was calculated from the area of the tie molecule distribution graph in which the x-axis was the molecular weight M and the y-axis was represented by n·P·dM. The corresponding graph is calculated from the GPC curve and DSC measurement results. With regard to the y-axis, n is the number of the polymer molecules having a molecular weight of M, which can be obtained as (dw/d log Mw)/M from the data of the GPC curve in which the x-axis is log Mw and the y-axis is dw/d log Mw. In addition, the P is a probability that the polymer molecules having a molecular weight of M form tie molecules, which can be calculated from the following equations 1 to 3, and the dM is an interval between the x-axis data (molecular weight M) of the GPC curve.

$$P = \frac{1}{3} \frac{\int_{2l_c+l_c}^{\infty} r^2 \exp(-b^2 r^2) dr}{\int_0^{\infty} r^2 \exp(-b^2 r^2) dr}$$ [Equation 1]

In Equation 1 above, r is an end-to-end distance of a random coil, $b^2$ is $3/2r^2$, $l_c$ is a crystal thickness, which is obtained from Equation 2 below, and $l_a$ is an amorphous thickness, which is obtained from Equation 3 below.

$$T_m = T_m^o \left(1 - \frac{2\sigma_e}{\Delta h_m l_c}\right)$$ [Equation 2]

In Equation 2 above, $T^o_m$ is 415K, ae is $60.9 \times 10^{-3}$ J/m², and $\Delta h_m$ is $2.88 \times 10^3$ J/m³.

$$l_a = \rho_c l_c (1-\omega^c)/\rho_a \omega^c$$ [Equation 3]

In Equation 3 above, $\rho_c$ is a crystal density, which is 1,000 kg/m³, $\rho_a$ is a density of amorphous phase, which is 852 kg/m³, $\omega^c$ is weight fraction crystallinity, which is confirmed from DSC results.

Calculation of entanglement molecular weight ($M_e$): Using a rotary rheometer, a storage elastic modulus and a loss elastic modulus of each sample were measured under conditions of a temperature of 150° C. to 230° C., an angular frequency of 0.05 to 500 rad/s and a strain of 0.5%, and from the plateau elastic modulus (GN0) thus obtained, the entanglement molecular weight was calculated according to Theoretical Equation below. However, in Theoretical Equation below, p means a density (kg/m³), R is the gas constant (8.314 Pa·m³/mol·K) and T is the absolute temperature (K).

$$M_e = (\rho RT)/G_N^0$$ [Theoretical Equation]

Content measurement and calculation of ultrahigh molecular weight component: In the molecular weight distribution analysis result of the sample, the area ratio (%) of the portion having a molecular weight of 1,000,000 or more relative to the total area was calculated.

Preparation Examples

Preparation Example 1: In a hexane slurry CSTR process, the resin was polymerized while supplying ethylene, hydrogen and 1-butene at a predetermined input rate using a metallocene catalyst capable of producing a bimodal molecular weight distribution. The prepared resin had a density of 0.9365 g/cm³ as measured according to ASTM D 1505 and an MI (melt index) of 0.02 as measured under conditions of 190° C. and 2.16 kg/10 min according to ASTM D 1238.

Preparation Example 2: A resin was prepared in the same manner as in Preparation Example 1, except that a metallocene catalyst of a different kind from that of Preparation Example 1 was used. The density of the prepared resin was 0.9396 g/cm³ and the MI was 0.26.

Preparation Example 3: A resin was prepared in the same manner as in Preparation Example 2, except that the input rate of the raw materials was controlled differently. The density of the prepared resin was 0.9392 g/cm³ and the MI was 0.34.

Preparation Example 4: A resin was prepared in the same manner as in Preparation Example 2, except that the input rate of the raw materials was controlled differently. The density of the prepared resin was 0.9358 g/cm³ and the MI was 0.75.

Preparation Example 5: A resin was prepared in the same manner as in Preparation Example 2, except that the input rate of the raw materials was controlled differently. The density of the prepared resin was 0.9363 g/cm³ and the MI was 0.27.

Preparation Example 6: A resin was prepared in the same manner as in Preparation Example 2, except that the input rate of the raw materials was controlled differently. The density of the prepared resin was 0.9396 g/cm³ and the MI was 0.32.

Preparation Example 7: A resin was prepared in the same manner as in Preparation Example 2, except that the input rate of the raw materials was controlled differently. The density of the prepared resin was 0.9365 g/cm³ and the MI was 0.60.

Preparation Example 8: A resin was prepared in the same manner as in Preparation Example 2, except that the input rate of the raw materials was controlled differently. The density of the prepared resin was 0.9367 g/cm³ and the MI was 0.47.

Preparation Example 9: A resin was prepared in the same manner as in Preparation Example 2, except that the input rate of the raw materials was controlled differently. The density of the prepared resin was 0.9369 g/cm³ and the MI was 0.38.

Preparation Example 10: A resin was prepared in the same manner as in Preparation Example 2, except that the input rate of the raw materials was controlled differently. The density of the prepared resin was 0.9364 g/cm³ and the MI was 0.48.

Preparation Example 11: A resin was prepared in the same manner as in Preparation Example 2, except that the density was 0.9362 g/cm³ and the MI measured under the same conditions was 0.43.

Preparation Example 12: A resin was prepared in the same manner as in Preparation Example 2, except that the density was 0.9363 g/cm³ and the MI measured under the same conditions was 0.26.

Preparation Example 13: A resin was prepared in the same manner as in Preparation Example 2, except that the density was 0.9362 g/cm³ and the MI measured under the same conditions was 0.44.

Preparation Example 14: A resin was prepared in the same manner as in Preparation Example 2, except that the density was 0.9363 g/cm³ and the MI measured under the same conditions was 0.39.

Examples

For the sample prepared in each of Preparation Examples, the content of tie molecules, the entanglement molecular weight and the content of the ultrahigh molecular weight component were measured according to the above methods. Alternatively, for the sample prepared in each of Preparation Examples above, the environmental stress crack resistance measured by FNCT was measured. The results are as shown in Table 3.

TABLE 3

| Example | Content of tie molecules (%) | Me (g/mol) | Content of ultrahigh molecular weight component (%) | FNCT (hour) | Remark |
|---|---|---|---|---|---|
| 1 | 12.2 | 1400 | 10.2 | 6500 | Excellent |
| 2 | 12.4 | 13900 | 2.8 | 2310 | Excellent |
| 3 | 10.6 | 19500 | 2.4 | 376 | Poor |
| 4 | 9.6 | 36700 | 2.0 | 59 | Poor |
| 5 | 11.3 | 15800 | 3.7 | 2000 | Excellent |
| 6 | 8.2 | 11700 | 5.2 | 1710 | Somewhat excellent |
| 7 | 9.5 | 35900 | 1.2 | 244 | Poor |
| 8 | 9.8 | 28200 | 1.2 | 285 | Poor |
| 9 | 9.5 | 23300 | 1.6 | 416 | Somewhat poor |
| 10 | 10.2 | 25100 | 1.3 | 114 | Poor |
| 11 | 11.0 | 23800 | 1.8 | 138 | Poor |
| 12 | 11.2 | 12500 | 2.8 | 1534 | Somewhat excellent |
| 13 | 10.6 | 25300 | 1.6 | 155 | Poor |
| 14 | 11.8 | 22800 | 1.4 | 168 | Poor |

Referring to Table 3 above, it can be seen that if at least two conditions of the conditions defined in the present application are satisfied, a polymer for heater-piping having excellent long-term durability can be designed.

The invention claimed is:

1. A method for predicting long-term durability of a resin composition for piping comprising:
    collecting data of the resin composition, the data comprising a content (wt %) of tie molecules, an entanglement molecular weight ($M_e$), and a content (wt %) of a component having a mass average molecular weight ($M_w$) of 1,000,000 or more; and
    using Equation below to determine a value of long-term durability of the resin composition:

Long-term durability predicted value of resin composition=$a \times (X)^b \times (Y)^c \times (Z)^d$   [Equation]

wherein, a=386,600, b=4.166, c=−1.831, and d=1.769, X, Y and Z represent, in the resin composition, the content (wt %) of tie molecules, the entanglement molecular weight ($M_e$), and the content (wt %) of the component having the mass average molecular weight ($M_w$) of 1,000,000 or more, respectively, where X, Y and Z are used as dimensionless constants excluding their respective units.

2. The method according to claim 1, further comprising:
    determining the value of long-term durability by calculating through the Equation to evaluate a long-term durability of the resin composition.

3. The method according to claim 1, further comprising:
    comparing the value of long-term durability determined by calculating through the Equation for each resin composition of a plurality of resin compositions.

4. The method according to claim 1, wherein the resin composition comprises a polyolefin resin.

5. The method according to claim 4, wherein the polyolefin resin is a polymer of ethylene, butene, propylene or α-olefin monomers.

6. The method of claim 1, wherein the long-term durability is excellent when the long term durability predicted value of the resin composition calculated from the Equation is greater than 2000.

7. The method of claim 1, wherein the long term durability predicted value of the resin composition calculated from the Equation has a linear correlation with a value measured from a full notch creep test (FNCT).

* * * * *